(12) United States Patent
Dong et al.

(10) Patent No.: US 11,459,533 B2
(45) Date of Patent: Oct. 4, 2022

(54) DEVICE FOR CULTIVATING TISSUE SECTIONS

(71) Applicant: Robert Bosch Gesellschaft für Medizinische Forschung mbH, Stuttgart (DE)

(72) Inventors: Meng Dong, Stuttgart (DE); Matthias Schwab, Stuttgart (DE); Heiko van der Kuip, Rottenburg (DE)

(73) Assignee: Robert Bosch Gesellschaft Für Medizinische Forshung mbH, Stuttgart (DE)

( * ) Notice: Subject to any disclaimer, the term of this patent is extended or adjusted under 35 U.S.C. 154(b) by 255 days.

(21) Appl. No.: 16/632,458

(22) PCT Filed: Jul. 13, 2018

(86) PCT No.: PCT/EP2018/069067
§ 371 (c)(1),
(2) Date: Jan. 20, 2020

(87) PCT Pub. No.: WO2019/029947
PCT Pub. Date: Feb. 14, 2019

(65) Prior Publication Data
US 2020/0231916 A1    Jul. 23, 2020

(30) Foreign Application Priority Data
Aug. 10, 2017   (DE) .................... 10 2017 213 923.4

(51) Int. Cl.
*C12M 3/00*      (2006.01)
*C12M 1/34*      (2006.01)

(52) U.S. Cl.
CPC ............ *C12M 21/08* (2013.01); *C12M 23/46* (2013.01); *C12M 41/34* (2013.01)

(58) Field of Classification Search
None
See application file for complete search history.

(56) References Cited

U.S. PATENT DOCUMENTS 5,073,504 A * 12/1991 Bogen ................. G01N 1/312
                                                    422/523
5,427,742 A *  6/1995 Holland .................. G01N 1/36
                                                    422/547
(Continued)

FOREIGN PATENT DOCUMENTS

CN       103743899 A  *  4/2014  ............... G01N 1/31
DE    10 2013 203 306 A1     8/2014
(Continued)

OTHER PUBLICATIONS

Document entitled Detachable and Adjustable Slide Incubator Volume machine translation of CN 103743899 A provided by Clarivate Analytics, original document published 2014 (Year: 2014).*
(Continued)

*Primary Examiner* — Holly Kipouros
(74) *Attorney, Agent, or Firm* — Maginot, Moore & Beck LLP

(57) ABSTRACT

A device for cultivating tissue sections, in particular for testing active ingredients and/or medications, includes a frame, at least one carrier component designed to hold a tissue section, and at least one liquid-absorbing strip element. The frame is designed to hold the at least one carrier component and the at least one strip element. A cultivation system includes the device for cultivating tissue sections and a holding vessel. The device can be used for testing active ingredients or medications on a tissue (section).

14 Claims, 6 Drawing Sheets

(56) References Cited

U.S. PATENT DOCUMENTS

| | | | |
|---|---|---|---|
| 2003/0180942 A1* | 9/2003 | Van Der Merwe | C12M 41/22 435/299.1 |
| 2007/0048732 A1 | 3/2007 | Park | |
| 2007/0116612 A1* | 5/2007 | Williamson, IV | G01N 1/36 422/400 |
| 2008/0206807 A1* | 8/2008 | Duymelinck | B01L 3/508 435/40.5 |
| 2010/0047853 A1 | 2/2010 | Kuo et al. | |
| 2010/0075410 A1* | 3/2010 | Desai | G01N 1/36 422/400 |
| 2011/0287982 A1 | 11/2011 | Stoppini | |
| 2012/0295299 A1* | 11/2012 | Gazenko | G01N 33/569 435/287.1 |

FOREIGN PATENT DOCUMENTS

| | | |
|---|---|---|
| DE | 10 2014 222 547 B3 | 2/2016 |
| EP | 0 842 262 B1 | 10/2002 |
| EP | 1 260 265 A1 | 11/2002 |
| EP | 1 857 543 A1 | 11/2007 |
| EP | 2 230 297 A1 | 9/2010 |
| EP | 2 420 569 A1 | 2/2012 |
| EP | 3 147 349 A1 | 3/2017 |
| JP | 9-292466 A | 11/1997 |
| WO | 2006/134432 A2 | 12/2006 |

OTHER PUBLICATIONS

International Search Report corresponding to PCT Application No. PCT/EP2018/069067, dated Nov. 6, 2018 (German and English language document) (10 pages).

Hickman, J. A. et al., "Three-dimensional models of cancer for pharmacology and cancer cell biology: Capturing tumor complexity in vitro/ex vivo," Biotechnology Journal, vol. 9, pp. 1115-1128, 2014, Wiley-VCH Verlag GmbH & Co. KGaA, XP55251805 (14 pages).

Database WPI, Week 199804, Thomson Scientific, London, GB; AN 1998-038286, XP002785946.

"Meilenstein in der Langzeitkultivierung von Gewebe gesetzt." Universität Leipzig, Apr. 26, 2012, accessed from Internet: https://www.bionity.com/de/news/137654/meilenstein-in-der-langzeitkultivierung-von-gewebe-gesetzt.html, XP002785945 (2 pages).

Van Der Kuip, H. et al., "Short term culture of breast cancer tissues to study the activity of the anticancer drug taxol in an intact tumor environment," BMC Cancer, BioMed Central, vol. 6:86, pp. 1-11, Apr. 7, 2006 (11 pages).

Carpenter, J., "New Measurements of Oxygen Solubility in Pure and Natural Water," Limnol Oceanogr., 11 (2), pp. 264-277, 1966 (14 pages).

Roskelley, C. D. et al., "The dominance of the microenvironment in breast and ovarian cancer," Seminars in Cancer Biology, vol. 12, pp. 97-104, 2002, Elsevier Science Ltd. (8 pages).

Bissell, M. J. et al., "Putting Tumors in Context," Nature Reviews, vol. 1, pp. 46-54, Oct. 2001, Macmillan Magazines Ltd. (9 pages).

Arrowsmith, J., "Phase III and submission failures: 2007-2010," Nature Reviews, vol. 10, Feb. 2011, Macmillan Publishers Limited. (1 page).

Östman, A., "The tumor microenvironment controls drug sensitivity," Nature Medicine, vol. 18, No. 9, pp. 1332-1334, Sep. 2012, Nature America, Inc. (3 pages).

Martin, Lawrence. All You Really Need to Know to Interpret Arterial Blood Gases. 2nd ed. Philadelphia: Lippincott Williams & Wilkins. 1999. Chapters 1, 2, & 5; pp. 1-26 & 68-82.

* cited by examiner

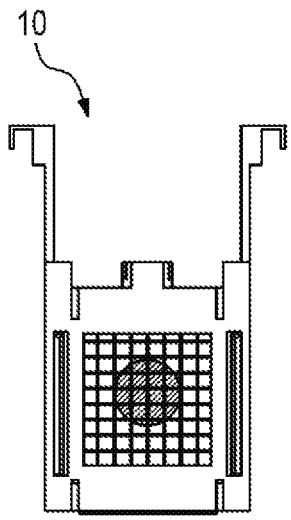 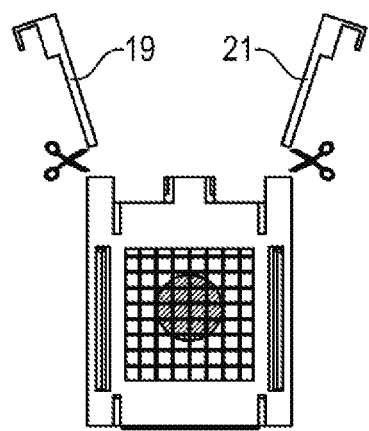 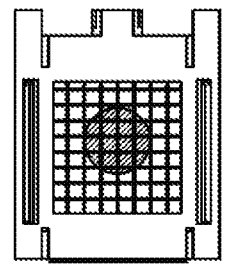
Fig. 4A   Fig. 4B   Fig. 4C
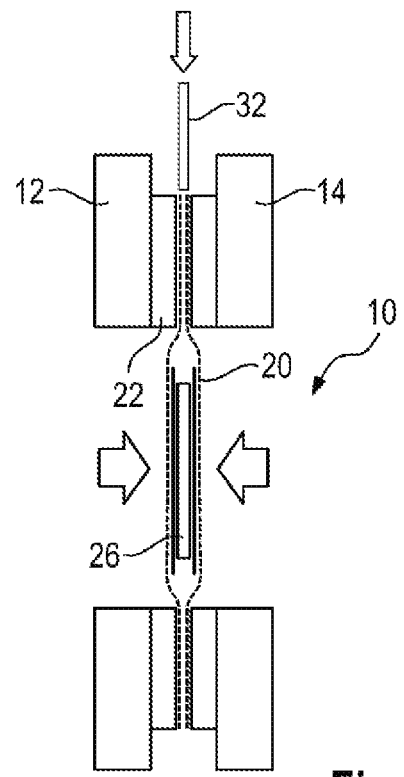
Fig. 5

DEVICE FOR CULTIVATING TISSUE SECTIONS

This application is a 35 U.S.C. § 371 National Stage Application of PCT/EP2018/069067, filed on Jul. 13, 2018, which claims the benefit of priority to Serial No. DE 10 2017 213 923.4, filed on Aug. 10, 2017 in Germany, the disclosures of which are incorporated herein by reference in their entirety.

The present disclosure relates to a device for the culturing of tissue sections, especially tumor tissue sections, for medicament testing.

BACKGROUND

In many areas of scientific research and diagnostics and in preclinical experiments, there is a great need for model systems of complex arrangements of cells that, for example, make it possible to test the toxicity and/or the metabolism of active ingredients or medicaments in vitro. Especially in the case of the testing of active ingredients on tumors, reproducible model systems are extremely important, since more than 90% of the antitumor medicaments tested successfully in preclinical in vitro and in vivo models fail in clinical trials, and approx. 66% are not therapeutically usable owing to lack of efficacy in the human body (Arrowsmith (2011) "Trial watch: Phase III and submission failures: 2007-2010". *Nature Reviews. Drug discovery*, 10, 87). This enormous error rate provides convincing evidence that the model systems currently used, which are used for medicament testing, fail to adequately reflect the situation of tumors in patients.

Human solid tumors are not just an accumulation of autonomous tumor cells, but, on the contrary, complex organ-like tissues composed of tumor cells and stromal cells (tumor-associated fibroblasts and inflammatory cells) which are embedded in an extracellular matrix and are supplied by an endothelial vascular system. The cellular microenvironment of a tumor cell is thus an integral and essential constituent of a tumor and plays a central role in tumorigenesis (Bissell, M. J. et al. (2001) "Putting tumors in context". *Nature Reviews. Cancer*, 1, 46-54), in tumor progression and metastasis (Roskelly et al. (2002) "The dominance of the microenvironment in breast ovarian cancer". *Seminars in Cancer Biology*, 12, 97-104) and also in sensitivity with respect to antitumor medicaments (Östmann (2012) "The tumor microenvironment controls drug sensitivity". *Nature Medicine*, 18, 1332-1334).

The action of an antitumor medicament on the entire tumor is thus crucially influenced not only by the intrinsic sensitivity of the tumor cell itself, but also by the cellular microenvironment of the tumor cell.

The development of novel preclinical models which can reflect this complex situation in the tumor better than those available at the moment is of prominent interest for research, diagnostics and especially the pharmaceutical industry, but also for individual sensitivity testing (individualized tumor therapy).

With the direct culturing of precisely cut tumor tissue slices obtained from surgical material, it is possible to largely maintain the individual tumor tissue ex vivo (Hickman et al. (2014) "Three-dimensional models of cancer for pharmacology and cancer cell biology: capturing tumor complexity in vitro/ex vivo." *Biotechnology Journal*, 9, 1115-1128; van der Kuip et al. (2016) "Short term culture of breast cancer tissues to study the activity of the anticancer drug taxol in an intact tumor environment." *BMC Cancer*, 6, 86), completely in contrast to all hitherto available preclinical models.

Various methods are known and have been successfully established for the culturing of such tumor sections, and what is common to all hitherto available methods is that said culturing is only possible for a very limited time and the tumor cell dies after a few days. On the basis of conventional culturing techniques, medicaments are thus tested on tissue which is dying per se, and this in turn raises doubt about the reliability of this system as a preclinical model. This very time-limited culturability is attributable to the fact that removal of the tumor inevitably leads to a complete cut-off of the blood supply and that supplying physiological concentrations of oxygen to the tumor tissue cultured in medium ex vivo is very difficult.

This is due to the different oxygen uptake capacity in culture medium in comparison with blood. For instance, oxygen-saturated water contains 0.28 mmol/L oxygen ($O_2$) under normal atmospheric conditions at a pressure of 1 atm and a temperature of 25° C. (Carpenter (1966) "New measurements of oxygen solubility in pure and natural water". *Limnol Oceanogr.*, 11 (2): 264-277), this value being even somewhat lower in medium owing to the salt content. In blood, oxygen is mainly (to an extent of about 98%) transported in the erythrocytes, bound reversibly to hemoglobin (Hb). Hemoglobin is loaded with up to 1.34 ml/g oxygen in the capillaries of the lungs and can then release the oxygen in the capillary areas of the organs and tissues of the body. The total oxygen content in arterial blood is, at 8.47 mmol/L (at a partial pressure of 100 mmHg), comparable with that of air (8.6 mmol/L at a partial pressure of 159 mmHg). Even in venous blood, the oxygen content is still 5.3 to 6.2 mmol/L (at a partial pressure of 40 mmHg; Martin (1999) "All You Really Need to Know to Interpret Arterial Blood Gases" LWW; Second edition, ISBN-10: 0683306049). Thus, this gas transport mechanism means that blood provides about 10 times more oxygen than oxygen-saturated medium.

In tissue, oxygen uptake in vivo depends on the partial pressure prevailing there: if said pressure is high, such as in the lungs for example, oxygen is taken up into the blood. In most tumor tissues, the partial pressure of oxygen is very low, meaning that a particularly large quantity of oxygen is released here from the blood into the tissue. This cannot be achieved by oxygen-saturated medium. In tumor tissues in a conventional liquid culture, cut-off of the blood supply thus leads to an acute undersupply of oxygen, to a reduction in cellular respiration and, associated therewith, to cellular stress and ultimately cell death.

Although the known systems can remedy this shortcoming in part with culturing devices for tissues at the air-liquid interface by exposing one side of tissue to air, making this type of culturing of tissue sections clearly superior to liquid culture, said systems lead to the formation of an artificial gradient oriented from the air side to the medium side, specifically such that only the upper cell layers facing the air correspond, in terms of their morphology and constitution, to the original tissue from which the tumor sections were obtained, whereas the cell layers facing away from the air exhibit signs of hypoxia and necrosis.

SUMMARY

Against this background, it is an object of the present disclosure to provide a device which can reduce or completely avoid the aforementioned disadvantages from the prior art.

According to the disclosure, this and other goals are achieved by a device for the culturing of tissue sections, especially for the testing of active ingredients and/or medicaments, the device having the following: a frame with an enclosing profile and a central free space formed by the enclosing profile, at least one support component, the support component being configured to accommodate a tissue section, and at least one liquid-absorbing strip element, wherein the frame is configured to hold the at least one support component and the at least one strip element, specifically such that the at least one strip element is mounted in the region of the enclosing profile and that the at least one support component is held on the frame with spanning of the free space and overlapping of the at least one strip element.

Furthermore, this and other goals are achieved by a culturing system for the culturing of tissue sections, wherein the culturing system has a device according to the disclosure and an accommodation vessel into which the device for the culturing of tissue sections and optionally testing of active ingredients and/or medicaments can be accommodated.

The object underlying the disclosure is completely achieved in this way.

What is achieved by the device according to the disclosure is that the tissue section is supplied with optimal oxygen concentrations on both sides, with an atmospheric culturing of the tissue section being made possible as a result. What can further be made possible with the device according to the disclosure is a constant perfusion with medium which can be guided past both sides of the tissue section, with the supply of nutrients and a uniform administration of medicaments being ensured as a result.

The device according to the disclosure allows the testing of active ingredients and medicaments while maintaining the native individual tissue, for example a tumor tissue, under largely physiological conditions. The total quantity of perfusate and thus the consumption of the active ingredient to be tested can be kept low, too.

In this connection, an "enclosing profile and a central free space formed by the enclosing profile" is understood here to mean any edging which is suitable for holding or stabilizing one or more support components clamped or accommodated in the (enclosing) frame.

Furthermore, a liquid-absorbing strip element is understood here to mean any element which consists of a (liquid-) absorbent material or has such a material and which can take up and optionally forward a liquid.

In a preferred embodiment of the device according to the disclosure, the frame comprises two frame members, each with an enclosing member profile and a central member free space formed in each case by the enclosing member profile. The two frame members are assemblable in a covering manner to form the frame by means of a connecting element, the connecting element preferably being configured as a click connection, guide rails, clamp connection or as a clasp.

Said embodiment offers the advantage that the at least one support component and the at least one strip element can be simply placed between the two frame members, which can be locked in position between the two frame members as a result of clipping or plugging them together.

The frame, or the two frame members, is/are, in this connection, preferably altogether substantially rectangular or flat block-shaped and has/have accordingly four sides.

In a further embodiment, the frame has a duct for the supply of liquid.

Said duct is, in a preferred embodiment, formed by connecting, or fitting together, the two frame members. Alternatively, the duct is situated on one of the two members.

Advantageously, a liquid, for example medium or a liquid which has an active ingredient to be tested or a medicament to be tested, can be supplied to the device—and thus to the tissue section to be cultured in the device—via the duct and the tissue can thus be perfused with the liquid. In this process, the liquid is taken up by the strip element and forwarded to the strip element-covering support component, where the liquid comes into contact with the tissue held therein.

In a preferred embodiment of the device according to the disclosure, the frame and/or the frame members has means for fixing of the strip element. Said means can be, for example, slit-shaped recesses in the member profile or in the sides of the frame members, into which recesses the at least one strip element is introduced and held.

The frame members—or just one frame member in another embodiment—can, in a preferred embodiment, each have on one of their sides a means for hanging of the device, via which it is for example possible to then hang the frame in the assembled state into an accommodation vessel.

In this connection, the hanging element can be, for example, an outwardly pointing hanger in each case.

For the device according to the disclosure, what can be further provided is that the at least one strip element is configured as sheet-shaped blotting paper.

In a further embodiment, the at least one support component is configured from a material selected from the group consisting of cotton fabric, nylon fabric, polycarbonate, cellulose hydrogel, animal intestine, especially pig intestine, 3D-printed biomaterials, especially 3D-printed alginate fabric or 3D-printed collagen fabric.

Preferably, the at least one support component is a latticed and oxygen-permeable fabric or has such a fabric.

In a preferred embodiment, the frame is configured from a solvent-resistant material.

In a preferred embodiment of the device according to the disclosure, the frame is formed from two frame members, and each of the two frame members has respectively two strip elements which are each mounted on opposite sides of a member profile and has respectively one support component which is held on a frame member in each case with spanning of the respective member free space and overlapping of the two strip elements.

This embodiment has the advantage that the tissue to be investigated or to be cultured, for example a thin tissue section and especially a tumor tissue section, can be held between the two support components when the two frame members are clipped or plugged together to form the frame.

Preferably, the distance between the two frame members in the assembled state of the frame is, in this connection, approx. 0.8 mm to approx. 2.2 mm, especially approx. 1.0 to approx. 2.0 and preferably approx. 1.6 mm. This makes it possible to insert the strip elements in each case, preferably on opposite sides of a rectangular or block-shaped frame member and especially on the upper and lower side in the case of vertical positioning/hanging of the device.

The strip element, or the blotting paper, has, in this connection, preferably a thickness of approx. 0.4 to approx. 1.2 mm, especially of approx. 0.8 mm.

The strip element is preferably sterile and autoclavable.

According to the disclosure, at least one support component is situated between the strip elements mounted on the member profiles, the support component spanning the free space.

In a further embodiment, the enclosing profile of the first frame member and the enclosing profile of the second frame member has means for the connection, for example plug-connection, of the two members. In a preferred embodiment, the first frame member has, in this connection, longitudinal recesses in opposing sides of the enclosing profile, which recesses are dimensioned such that longitudinal elevations of the second frame member can be accommodated or plugged therein, which elevations are provided on opposite sides of the enclosing profile of the second frame member. What is thus achieved is that, by placing the two frame members together or on top of one another, the connection means respectively interlock and the two frame members can be plugged together and fixed as a result.

As already mentioned further above, the present disclosure also relates to a culturing system for the culturing of tissue sections, especially for the testing of active ingredients and/or medicaments, wherein the culturing system has a device according to the disclosure as described above and an accommodation vessel, the device being introducible into the accommodation vessel, preferably in a vertically hanging or upright manner.

Said embodiment has the advantage that, for example, a conventional vessel, especially a ventilatable tube, for example an appropriately dimensioned centrifuge tube, can be used as an accommodation vessel into which the device according to the disclosure can be hanged, for example via the means for hanging of the device. The tube can, in this connection, have a screw cap which allows a sterile gas exchange and allows access to the duct for the supply of liquid, for example through a septum slit. The closability of the tube with the screw cap is, at the same time, not impaired.

The tube can, in a preferred embodiment, be selected from a tube holding between 10 and 100 ml and especially a 10, 15, 20, 30, 40, 50, 60, 70, 80, 90 or 100 ml tube.

Preferred dimensions for the frame are between approx. 18 mm to approx. 28 mm×21 mm to approx. 31 mm, especially approx. 23× approx. 26 mm, and also, for the free space, approx. 9 mm to approx. 19 mm× approx. 10 mm to approx. 20 mm, especially approx. 14× approx. 15 mm.

This system according to the disclosure advantageously achieves a vertical orientation of the device according to the disclosure in the accommodation vessel and thus also a vertical orientation of the tissue/tissue section in a closed, sterile-ventilatable accommodation vessel. The system can then, for example, be kept in an incubator under a controlled atmosphere.

Furthermore, in the case of a vertical orientation, the device is preferably accommodated in the accommodation vessel such that a duct for the supply of liquid, for example by means of a perfusion needle, is on the upper side of the frame, which duct is optionally connected to perfusion tubing. In a preferred embodiment, said tubing can be connected to a syringe and be under the control of a syringe pump, via which a controlled perfusion is possible. In the accommodation vessel, the liquid introduced via this system can be collected in the collection vessel at the bottom after passing through the support component and thus also the tissue.

The present disclosure thus also relates to the use of the device according to the disclosure as described above or of the described culturing system according to the disclosure for the culturing of tissues and/or tissue sections for the testing of active ingredients and/or medicaments.

Accordingly and overall, the present disclosure provides a simple-to-handle modular device which makes it possible to directly culture precisely cut (tumor) tissues with microperfusion in a very thin layer of culture medium and to expose said tissues to a gas atmosphere of defined composition. The present disclosure can thus provide both physiologically relevant oxygen concentrations and physiologically relevant perfusion rates during culturing.

In addition, the present device according to the disclosure and the culturing system according to the disclosure make it possible to test medicaments on individual tumors ex vivo while maintaining physiologically relevant characteristics, such as a largely intact microenvironment and adjusted oxygen concentration.

In comparison with conventional preclinical in vitro and in vivo models, but also tissue cultures already used, it is possible with the aid of the device according to the disclosure to provide conditions which make it possible to ascertain sensitivity and resistance with respect to medicaments in individual patient tumors very much more precisely.

According to the disclosure, tissues or tissue sections can be accommodated in the support component, especially tumor tissue sections, especially from tumors of a human. The tumor can, in this connection, be a benign or malignant tumor of any tissue, especially a solid tumor, which is, in particular or for example, selected from the group comprising tumors of the respiratory organs, tumors of the digestive organs, breast cancer, ovarian cancer, prostate cancer, malignant melanoma.

In one embodiment, the tissue is selected from a tissue from lung, larynx, breast, stomach, pancreas, prostate, bladder, ovary, skin, kidney, sinus, large intestine, intestine, rectum, esophagus, heart, spleen, brain and the coverings thereof, spinal cord and the coverings thereof, muscle, connective tissue, adrenal gland, parathyroid, thyroid, uterus, testes, pituitary gland, reproductive organs, liver, gall bladder, eye, ear, nose, throat, tonsils, mouth and lymph nodes.

In terms of its use, the present disclosure is not limited to the details of the establishment and arrangement of the components that are presented in the description or illustrated in the drawings. The disclosure allows other embodiments and can be carried out in various ways. In addition, the manner of expression and terminology used here serves for descriptive purposes and is not to be considered restrictive. In the present text, the use of "inclusive of", "comprising" or "having", "containing", "including" and variations thereof is intended to encompass what is listed afterwards and also equivalents thereof and additions.

The present disclosure is further illustrated by the following examples, which are in no way to be understood as further restrictive. The entire content of all information cited in the present application (inclusive of literature references, granted patents, published patent applications and copending patent applications) is hereby expressly incorporated into the present text by reference. In the event of a conflict, the present description, inclusive of any definitions herein, has priority.

BRIEF DESCRIPTION OF THE DRAWINGS

FIGS. 4A to 4C show the step-by-step preparation for the utilization of the device according to the disclosure in a tissue embedding cassette;

FIG. 5 shows a longitudinal section of the device according to the disclosure;

DETAILED DESCRIPTION

Figure 1A:
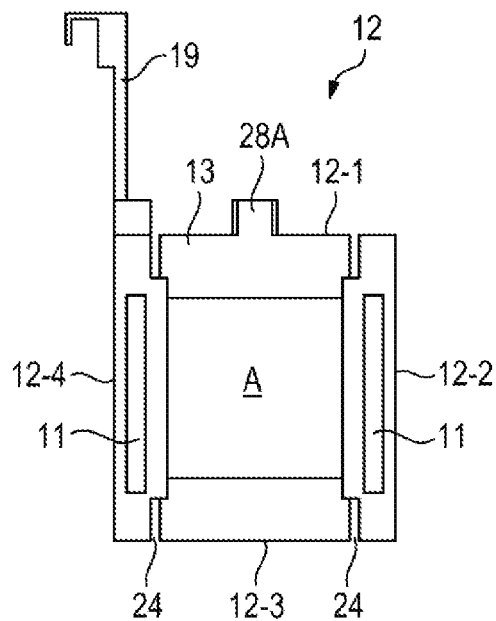
FIGS. 1A to 1D show the individual constituents of one exemplary embodiment of the device according to the disclosure.
Figure 1B:
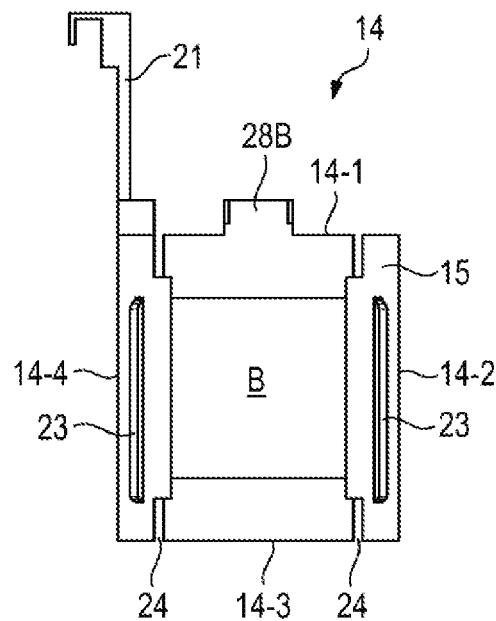

In the figures, the reference sign 10 shows overall one embodiment of a device according to the disclosure for the culturing of tissue sections. In this connection, FIGS. 1A and 1B show two frame members 12 and 14, which form the frame 16 as a result of their assembly (see, for example, FIGS. 2D and 3A).

Figure 2A:
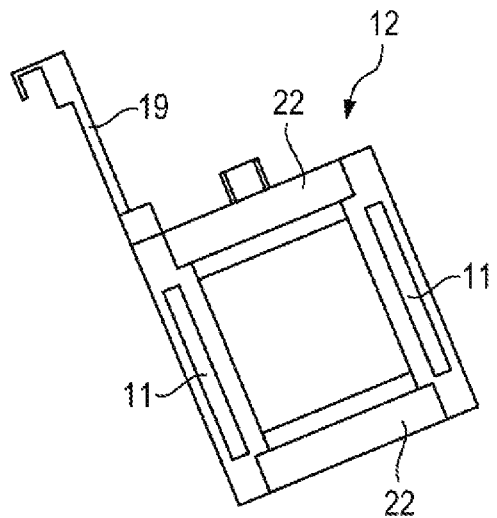
FIGS. 2A to 2D show the individual constituents of the device according to the disclosure and the fitting thereof together in a step-by-step manner to form the device according to the disclosure.
Figure 2B:
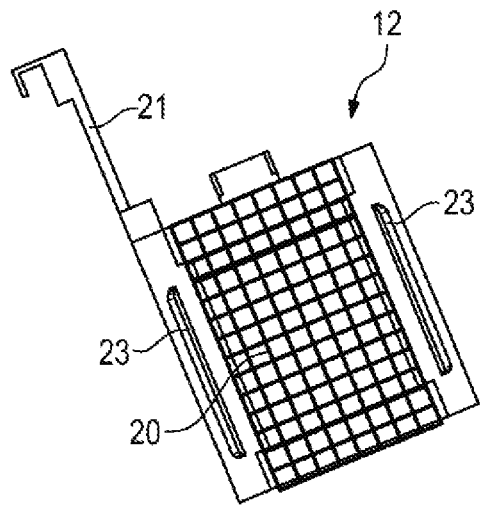
Figure 2C:
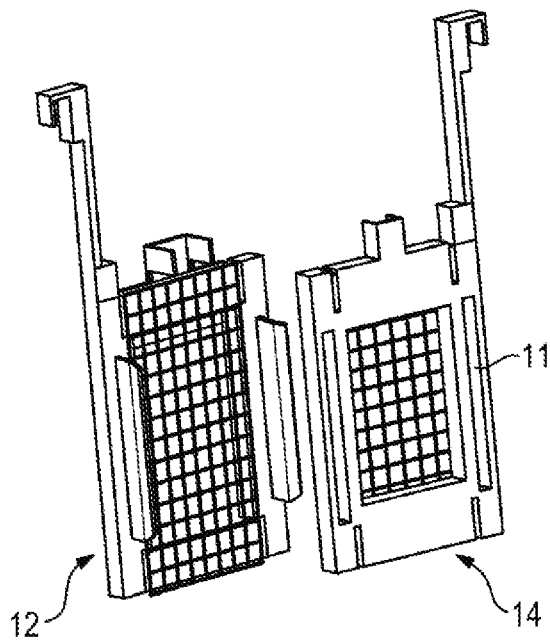
Figure 2D:
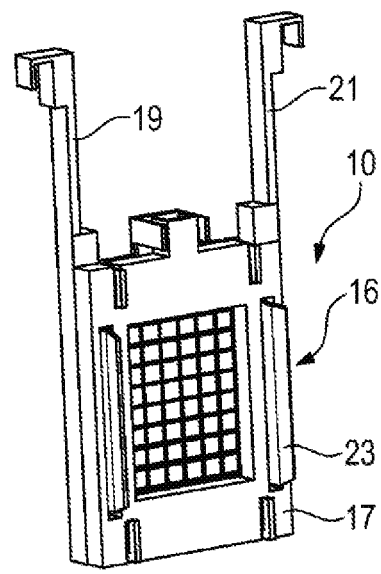
Figure 3A:
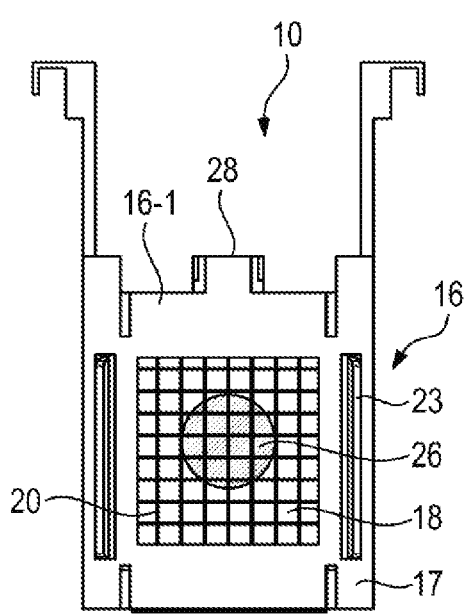
FIGS. 3A to 3C show the individual constituents of the culturing system according to the disclosure for the culturing of tissue sections.

The frame 16 has an enclosing profile 17 and also a free space 18 formed by the enclosing profile 17, which free space is spanned by a support component 20 in FIGS. 2D and 3A.

Each of the frame members 12 and 14 has a substantially rectangular or flat-block shape with an enclosing profile 13 and 15, respectively, and with four sides 12-1, 12-2, 12-3, 12-4 and 14-1, 14-2, 14-3, 14-4, respectively. Situated in the center in both cases are the free spaces A and B, which form the free space 18 of the frame 16 as a result of fitting together the two frame members 12 and 14.

Furthermore, the two frame members 12 and 14 have, respectively on the corner of the side 12-1 and 14-1, a means for hanging 19 and 21 of the device 10.

Figure 1C:
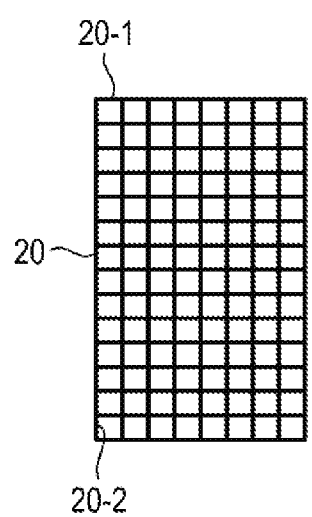
Figure 1D:
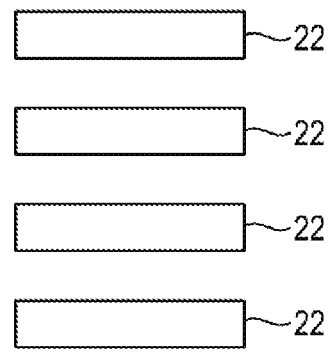

FIG. 1C shows an isolated support component 20 and FIG. 1D shows four strip elements 22.

What can be further gathered from the figures is that the first frame member 12 has, on two opposing sides 12-4 and 12-2 in the enclosing profile 13, recesses 11 in both cases, which are designed to accommodate, for example by plugging together, the shape of the slit-shaped elevations 23 matching recesses 11. Said slit-shaped elevations 23 are situated on opposing sides 14-4 and 14-2 in the enclosing profile 15 of the second frame member 14.

The strip elements 22 are mounted on the member profile 13 on opposite sides 12-1 and 12-3 of the frame member 12 and on the member profile 15 on opposite sides 14-1 and 14-3 of the frame member 14 (shown in FIGS. 2A and 2B for the frame member 12), specifically via means for fixing 24 which are provided on the frame members 12, 14 and which are slits in the member profile on opposite sides 12-1, 12-3 and 14-1, 14-3, respectively, in the example shown in the figures. What is then placed over the strip elements 22 is a support component 20 in each case, which spans the free space A, B or 18 and which, with two of its sides 20-1 and 20-2, projects beyond the strip elements 22 or is placed on top thereof (see FIG. 2B).

FIG. 2C shows the two assembled frame members 12, 14, which were assembled in both cases in line with the description of FIGS. 2A and 2B. The two frame members 12, 14 are then assembled to form the frame 16 (see FIG. 2D) such that the means for hanging 19, 21 are situated on opposite sides of the frame 16, and the support components 20, which are mounted on the frame member 12 and on the frame member 14, are situated between the strip elements 22 in the assembled frame 16.

FIG. 3A shows one exemplary embodiment of an assembled device 10 according to the disclosure having a tissue section 26 held in the support component.

What can be further gathered from FIG. 3A is that the frame 16 has a duct 28 for the supply of liquid as a result of fitting together the frame members 12, 14, which duct is situated on the side 16-1 of the frame. Said duct 28 is formed by fitting together the two "half" duct segments 28A and 28B (see FIG. 1A) of the frame members 12, 14.

Figure 3B:
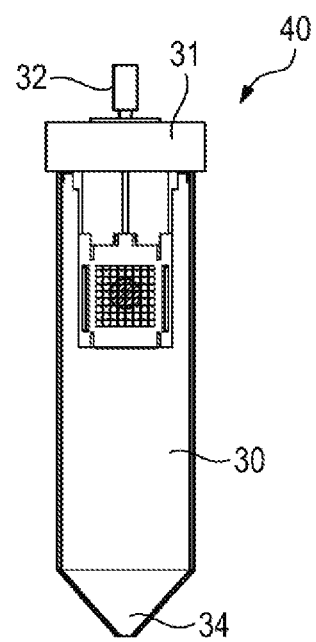

For the culturing of the tissue section 26, the device 10 according to the disclosure is introduced into an accommodation vessel 30 (see FIG. 3B), which is a tube with a screw cap 31 in the example shown in FIG. 3B. The device 10 and the accommodation vessel 30 form a culturing system 40 according to the disclosure. The tube is sterile-ventilatable via the screw cap, which has, for example, a septum slit (not shown). Via the screw cap 31, a perfusion needle 32 can be introduced into the accommodation vessel 30 into the duct 28 and, via the perfusion needle 32, liquid can be conducted to the device 10 present in the accommodation vessel 30 and thus via the strip elements 22 and the support component 20 to the tissue section 26. The supplied liquid can then be collected in the lower region 34 of the accommodation vessel 30 and optionally analyzed after culturing.

Figure 3C:
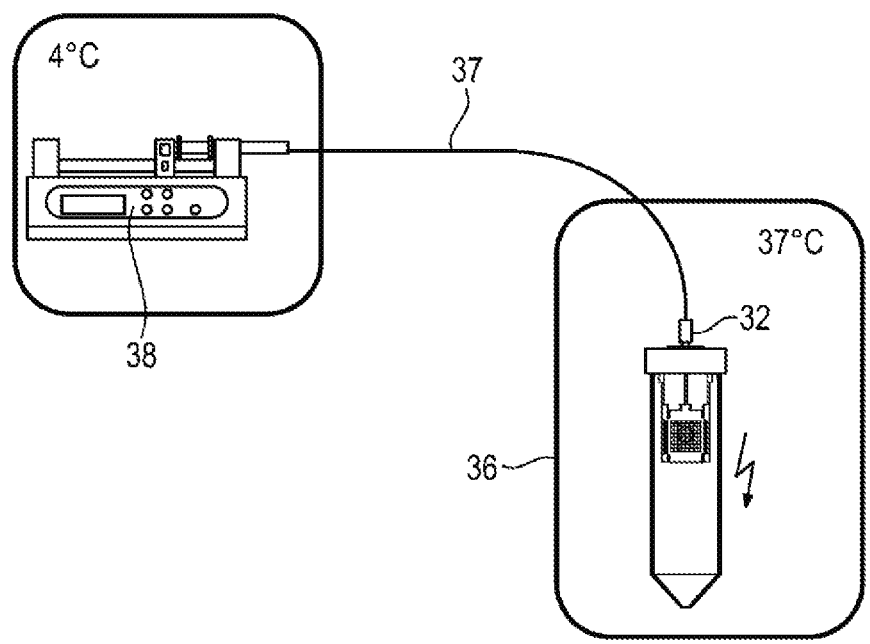

FIG. 3C depicts how a controlled supply of liquids can be performed: The culturing system 40 is situated in an incubator 36 with a controlled atmosphere (the oxygen concentration is, for example, exactly regulated by a controlled supply of nitrogen into the incubator). The perfusion needle 32 is connected to tubing 37 which is guided out of the incubator 36, which is held here at 37° C. by way of example. The tubing 37 in turn is connected to a syringe pump 38 which, as a result of the activation thereof, can supply liquid, for example culturing medium and/or an active ingredient to be tested/medicament to be tested, via a syringe in a controlled and precise manner. This is held at 4° C. in the example shown in FIG. 3C.

FIG. 4 shows further advantageous handling of the device according to the disclosure in steps A to C: by simply cutting off the means for hanging 19, 21, the tissue section situated in the support component can be directly fixed and be subsequently investigated or subjected to further investigations in a simple manner. In this connection, the frame dimensions preferred in one embodiment are, at approx. 23 x approx. 26 mm, conceived such that the frame fits into standard embedding cassettes for biopsies (external dimensions: L 40×W 28×H 6.8 mm) after the means for hanging have been cut off.

FIG. 5 shows a longitudinal section through the center of the device 10 according to the disclosure. What can be seen is that the support component 20 is sandwiched between the strip elements 22 in the region of the member profiles 13 and 15 of the frame members 12, 14. The tissue section 26 in turn is held between two support components 20 in the free space 18, meaning that the section is surrounded by the atmosphere and ultimately oxygen on both sides. In comparison with conventional culturing systems in which the tissue sections are positioned in an especially horizontal manner, this offers the major advantage that more oxygen is supplied to the tissue section and said tissue section can also take up more oxygen, and this in turn allows a distinctly improved tissue model.

Exemplary experimental procedure with the device according to the disclosure or the culturing system according to the disclosure Various embodiments of the device according to the disclosure were tested with respect to different support components, with respect to culturing periods of different length and with respect to different tissues/tissue sections.

The latticed support components composed of cotton or nylon with a relatively large lattice pore size (cotton: 500 µm, nylon: 89 µm) were tested. Furthermore, polycarbonate membranes with a small pore size (12 µm) were tested, as were a natural cellulose hydrogel (Xellulin®; Xellutec GmbH, Neuried, Germany), a support component composed of decellularized pig intestine and a support component composed of a 3D-printed alginate mesh or collagen mesh.

All the support components were found to be suitable materials for use in the device according to the disclosure (data discussed in part below).

Furthermore, different tissue sections, which were cultured for different lengths of time in the device according to the disclosure or the culturing system according to the disclosure, were further investigated. To this end, the devices according to the disclosure 10, which contained tissue sections 26, were removed from the accommodation vessel 30, the means for hanging 19, 21 were cut off and the devices 10, which contained the different tissue sections, were inserted into commercially available embedding cassettes for immunostaining with respect to certain markers.

Figure 6:
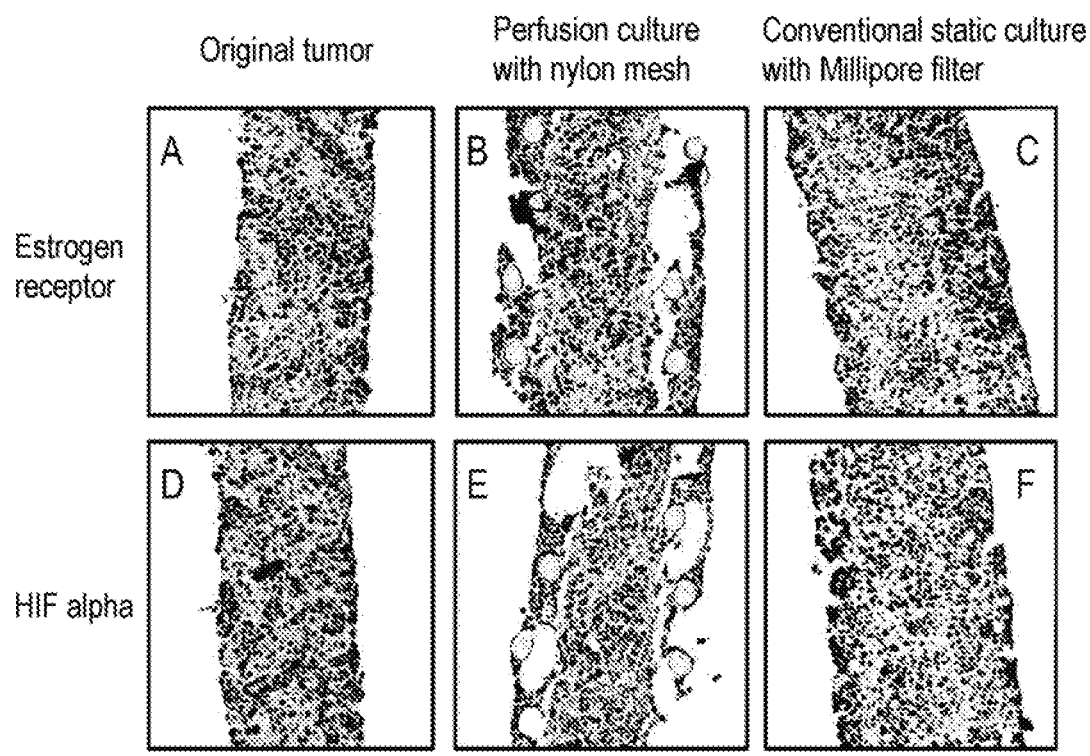
FIG. 6 shows images of estrogen receptor immunostaining and HIF1-alpha immunostaining of original tumor tissue sections (A, D), tumor tissue sections cultured beforehand with a device according to the disclosure (B, E) and tumor tissue sections cultured with a conventional culturing device (C, F)

The immunostainings discussed below revealed the practical handling of the device according to the disclosure with the embedding cassettes. Sections of an original tumor tissue were stained immunohistochemically with respect to the markers estrogen receptor and hypoxia-inducible factor 1 (HIF1) alpha. In comparison, tissue sections of the same tumor were cultured beforehand with the culturing system according to the disclosure for three days in each case, specifically with a nylon mesh, and alternatively with a conventional filter (Millicell® Cell Culture Inserts; Merck Millipore, PTFE, pore size 0.4 µm). The results of these culturing experiments are depicted in FIG. 6, and what was revealed thereby was that the tissue sections which were cultured by means of the culturing system according to the disclosure (FIG. 6B, E) have a similar morphology and biomarker expression to the original tumor tissue section (FIG. 6A, D). By contrast, the tumor tissue section which was cultured by means of the conventional device (FIG. 6C, F) showed an artificial gradient from the atmosphere side to the filter side with respect to the expression of the tumor biomarkers estrogen receptor and HIF1-alpha, and this results in an unbalanced cell culture model which is ultimately not as suitable for reliable in vitro medicament tests as the device according to the disclosure.

Figure 7:
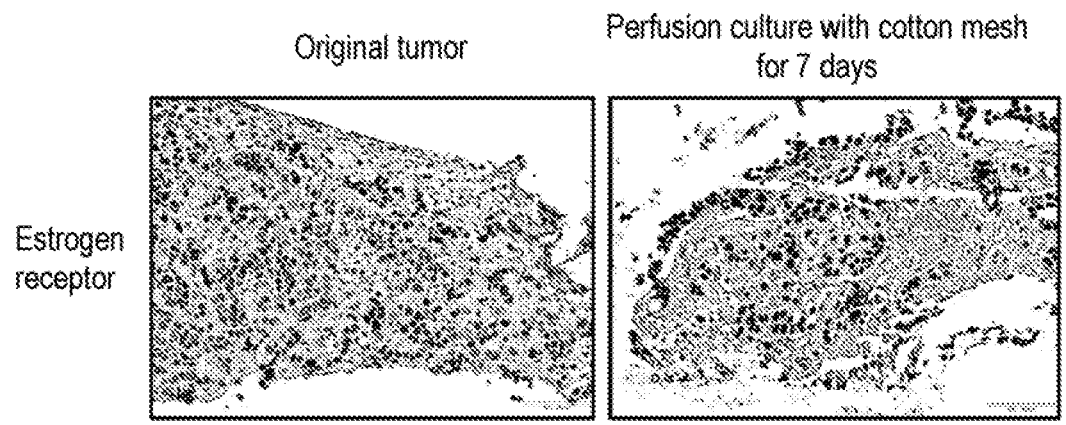
FIG. 7 shows images of estrogen receptor immunostaining of an original tumor tissue section (left) in comparison with a tumor tissue section cultured with the system according to the disclosure for 7 days (right)

Furthermore, further experiments showed that the device according to the disclosure can even be used for longer culturing experiments. The results of these series of experiments are shown in FIG. 7: even after a 7-day culturing period with the system according to the disclosure (FIG. 7, right), the tumor tissue section showed a similar morphology and biomarker expression to the noncultured original tumor (FIG. 7, left), and this was demonstrated by the stainings with respect to the estrogen receptor.

Figure 8:
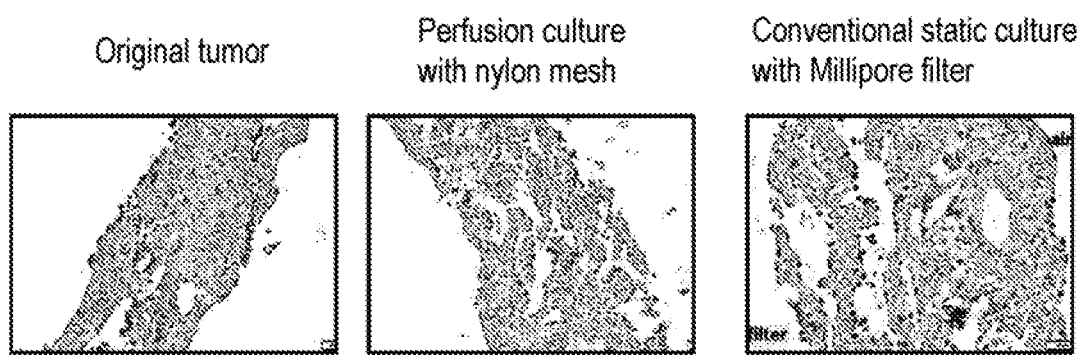
FIG. 8 shows images of HIF1-alpha immunostaining of an original lung tumor tissue section (left) in comparison with lung tumor tissue sections cultured beforehand with the system according to the disclosure (center) and cultured beforehand with a conventional filter system (right).

Lastly, primary tissue sections from a lung cancer patient were also cultured and stained immunohistochemically in a comparative manner. These results are shown in FIG. 8: shown on the left is the immunostaining for HIF1-alpha for the original tumor, shown in the center is the immunostaining of the section of the same tumor that was cultured for 5 days with the system according to the disclosure on a nylon mesh, and shown on the right is the immunostaining of a section of the same tumor that was cultured for 5 days with a conventional system (Millipore). It was revealed that the tissue section cultured with the system according to the disclosure showed the same morphology and HIF1-alpha expression as the original tumor tissue section, whereas the tissue section cultured on the conventional filter again showed a gradient from the atmosphere side to the filter side.

The experiments outlined above provide striking evidence of the distinct advantage offered by the culturing system according to the disclosure/the device according to the disclosure over the conventional devices and methods for culturing tissues/tissue sections.

The systems and devices according to the disclosure thus make it possible to test the action of medicaments on tumor tissue, even over relatively long periods, in a model which is reproducible and is comparable with the original tissue.

The invention claimed is:

1. A device for the culturing of tissue sections comprising:
a frame with an enclosing profile and a central free space formed by the enclosing profile;
at least one support component; and
at least one liquid-absorbing element supported by the frame,
wherein
the frame comprises a first frame member defining a first window therethrough, and a second frame member defining a second window therethrough,
the at least one support component comprises a first support component spanning the first window and a second support component spanning the second window,
the device is configured such that when assembled the device is configured to accommodate a tissue sample between the first support component and the second support component, at least a portion of the first support component is in direct opposition to at least a portion of the second support component, and the at least one liquid-absorbing element does not span the first window or the second window,
and
at least one of the first and second support components overlaps the at least one liquid-absorbing element.

2. The device as claimed in claim 1, wherein:
each of the first and second frame members include a respective enclosing member profile and a respective central member free space defined by the respective enclosing member profile, and
the first and second frame members are configured to be assembled with a connecting element in a covering manner to form the frame.

3. The device as claimed in claim 2, wherein:
a first and a second element of the at least one liquid-absorbing element are mounted on the first frame member on opposite sides of the first window;

a third and a fourth element of the at least one liquid-absorbing element are mounted on the second frame member on opposite sides of the second window;

the first support component overlaps the first and second liquid absorbing element; and the second support component overlaps the third and fourth elements.

4. The device as claimed in claim 2, wherein the connecting element is configured as one of a click connection, guide rails, a clamp connection, and a clasp.

5. The device as claimed in claim 1, wherein the frame has a duct configured for supply of liquid.

6. The device as claimed in claim 1, wherein the frame has a fixing element configured to fix the at least one liquid-absorbing element.

7. The device as claimed in claim 1, wherein the frame has a hanging arrangement configured for hanging the device.

8. The device as claimed in claim 1, wherein the at least one liquid-absorbing element is configured as sheet-shaped blotting paper.

9. The device as claimed in claim 1, wherein the at least one support component is formed of a material selected from the group consisting of cotton fabric, nylon fabric, polycarbonate, cellulose hydrogel, animal intestine, pig intestine, 3D-printed biomaterials, 3D-printed alginate fabric, and 3D-printed collagen fabric.

10. The device as claimed in claim 1, wherein the frame is formed of a solvent-resistant material.

11. The device as claimed in claim 1, wherein the device is configured for culturing the tissue sections for testing of at least one of active ingredients and medicaments.

12. A culturing system for the culturing of tissue sections comprising:

an accommodation vessel; and a device comprising:
    a frame with an enclosing profile and a central free space formed by the enclosing profile;
    at least one support component; and
    at least one liquid-absorbing element supported by the frame,
wherein
    the frame comprises a first frame member defining a first window therethrough, and a second frame member defining a second window therethrough,
    the at least one support component comprises a first support component spanning the first window and a second support component spanning the second window,
    the device is configured such that when assembled the device is configured to accommodate a tissue sample between the first support component and the second support component, at least a portion of the first support component is in direct opposition to at least a portion of the second support component, and the at least one liquid-absorbing element does not span the first window or the second window,
at least one of the first and second support components overlaps the at least one liquid-absorbing element, and
the device is configured to be introduced into and vertically hung in the accommodation vessel.

13. The culturing system as claimed in claim 12, wherein the accommodation vessel is a ventilatable tube.

14. The culturing system as claimed in claim 12, wherein the culturing system is configured for culturing the tissue sections for testing of at least one of active ingredients and medicaments.

* * * * *